US011446219B2

(12) United States Patent
Kohler Riedi et al.

(10) Patent No.: US 11,446,219 B2
(45) Date of Patent: Sep. 20, 2022

(54) METHODS AND KITS FOR REMOVING CALCULUS USING A NON-ENZYMATIC, HYDROGEN PEROXIDE DECOMPOSITION CATALYST

(71) Applicant: 3M INNOVATIVE PROPERTIES COMPANY, St. Paul, MN (US)

(72) Inventors: Petra L. Kohler Riedi, Minneapolis, MN (US); Evan Koon Lun Yuuji Hajime, Woodbury, MN (US); Chuntao Cao, Woodbury, MN (US); Ingo R. Haeberlein, Weilheim (DE); Joel D. Oxman, Minneapolis, MN (US); Steven P. Swanson, Blaine, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 697 days.

(21) Appl. No.: 16/342,106

(22) PCT Filed: Sep. 5, 2017

(86) PCT No.: PCT/US2017/050052
§ 371 (c)(1),
(2) Date: Apr. 15, 2019

(87) PCT Pub. No.: WO2018/075149
PCT Pub. Date: Apr. 26, 2018

(65) Prior Publication Data
US 2020/0179249 A1 Jun. 11, 2020

Related U.S. Application Data

(60) Provisional application No. 62/410,706, filed on Oct. 20, 2016.

(51) Int. Cl.
| | | |
|---|---|---|
| *A61Q 11/00* | (2006.01) | |
| *A61K 8/22* | (2006.01) | |
| *A61K 8/20* | (2006.01) | |
| *A61K 8/58* | (2006.01) | |
| *A61C 17/18* | (2006.01) | |

(52) U.S. Cl.
CPC .......... *A61K 8/22* (2013.01); *A61K 8/20* (2013.01); *A61K 8/58* (2013.01); *A61Q 11/00* (2013.01); *A61C 17/18* (2019.05); *A61K 2800/884* (2013.01); *A61K 2800/92* (2013.01)

(58) Field of Classification Search
CPC ...... A61Q 11/00; A61K 8/22; A61K 2800/92; A61K 2800/884; A61K 8/58; A61K 8/20
USPC ........................................................ 424/53
See application file for complete search history.

(56) References Cited

U.S. PATENT DOCUMENTS

| | | |
|---|---|---|
| 1,482,367 A | 1/1924 | Elledge |
| 3,372,125 A | 3/1968 | Hill |
| 3,535,421 A | 10/1970 | Briner |
| 3,678,154 A | 7/1972 | Widder |
| 4,155,868 A | 5/1979 | Kaplan |
| 4,381,247 A | 4/1983 | Nakagawa |
| 4,417,993 A | 11/1983 | Gergely |
| 4,522,805 A | 6/1985 | Gordon |
| 4,528,180 A | 7/1985 | Schaeffer |
| 4,894,220 A | 1/1990 | Nabi |
| 5,071,439 A | 12/1991 | Weible |
| 5,403,578 A | 4/1995 | Gordon |
| 5,670,138 A | 9/1997 | Venema |
| 5,908,614 A | 6/1999 | Montgomery |
| 5,965,110 A | 10/1999 | Arnold |
| 6,331,291 B1 | 12/2001 | Glace |
| 6,379,654 B1 | 4/2002 | Gebreselassie |
| 6,440,396 B1 | 8/2002 | McLaughlin |
| 6,485,709 B2 | 11/2002 | Banerjee |
| 6,669,929 B1 | 12/2003 | Boyd |
| 6,685,921 B2 | 2/2004 | Lawlor |
| 7,530,808 B2 | 5/2009 | Cao |
| 7,740,479 B2 | 6/2010 | Allred |
| 7,816,423 B2 | 10/2010 | Karim |

(Continued)

FOREIGN PATENT DOCUMENTS

| | | |
|---|---|---|
| CN | 104173197 | 12/2014 |
| DE | 1944308 | 3/1971 |

(Continued)

OTHER PUBLICATIONS

Putt et al., "Custom Tray Application of Peroxide Gel as an Adjunct to Scaling and Root Planing in the Treatment of Periodontitis: Results of a Randomized Controlled Trial after Six Months." J Clin Dent 2013;24:100-107 (Year: 2013).
Kraus et al., "Salivary Catalase and Peroxidase values in Normal Subjects and in Persons with Periodontal Disease." O.S, O.M, & O.P. Jan. 1958; vol. 11, No. 1; pp. 95-102 (Year: 1958).
Home Remedies, "Get Rid of Plaque & Tartar on Teeth with Natural Remedies," HomeRemedies.com, Oct. 30, 2009; 3 pages (Year: 2009).
"Iodide", Wikipedia, [retrieved from the internet on Jun. 12, 2019], URL <https://en.wikipedia.org/wiki/Iodide>, pp. 1-4.

(Continued)

*Primary Examiner* — Eisa B Elhilo
(74) *Attorney, Agent, or Firm* — 3M Innovative Properties Company

(57) ABSTRACT

Methods and kits for removing calculus from a tooth, wherein the method can include applying a component A to the tooth, wherein component A comprises a hydrogen peroxide or a precursor thereto; applying a component B to the tooth, wherein component B comprises a non-enzymatic, hydrogen peroxide decomposition catalyst for generating oxygen gas; wherein components A and B are applied simultaneously or sequentially to the tooth, thereby generating oxygen gas to soften and/or loosen at least part of the calculus on the tooth; and removing at least a part of the calculus from the tooth.

20 Claims, No Drawings

(56) References Cited

U.S. PATENT DOCUMENTS

| | | |
|---|---|---|
| 8,647,608 B2 | 2/2014 | Yang |
| 8,906,981 B2 | 12/2014 | Yang |
| 2002/0141949 A1 | 10/2002 | Banerjee |
| 2003/0194382 A1 | 10/2003 | Chang |
| 2004/0120900 A1 | 6/2004 | Arsenault |
| 2005/0196348 A1 | 9/2005 | Georgiades |
| 2006/0051385 A1 | 3/2006 | Scholz |
| 2006/0099155 A1 | 5/2006 | MacDonald |
| 2006/0198803 A1 | 9/2006 | Giniger |
| 2007/0231277 A1* | 10/2007 | Sharma .......... A61K 8/66 424/53 |
| 2009/0220919 A1 | 9/2009 | Yang |
| 2011/0305738 A1 | 12/2011 | Ladizinsky |
| 2012/0282234 A1 | 11/2012 | Min |
| 2013/0189201 A1* | 7/2013 | Buelo ............ A61K 8/24 424/53 |
| 2017/0367941 A1 | 12/2017 | Haeberlein |
| 2019/0231649 A1 | 8/2019 | Kohler Riedi et al. |

FOREIGN PATENT DOCUMENTS

| | | | |
|---|---|---|---|
| FR | 2787778 | 6/2000 | |
| GB | 1492660 | 11/1977 | |
| JP | 0597640 | 4/1993 | |
| JP | 2003-40754 | 2/2003 | |
| RU | 2432620 | 10/2011 | |
| WO | WO 1992-07550 | 5/1992 | |
| WO | WO 1998-43603 | 10/1998 | |
| WO | WO 1998-057653 | 12/1998 | |
| WO | WO 2009-109533 | 9/2009 | |
| WO | WO 2012-072777 | 6/2012 | |
| WO | WO 2013-055478 | 4/2013 | |
| WO | WO 2015-073246 | 5/2015 | |
| WO | WO 2016-099875 | 6/2016 | |
| WO | WO 2016/099875 A1 * | 6/2016 | ............ A61Q 11/00 |
| WO | WO 2017/223161 | 12/2017 | |
| WO | WO 2018-075149 | 4/2018 | |
| WO | WO 2018-075150 | 4/2018 | |

OTHER PUBLICATIONS

Bray, "Reactions Involving Hydrogen Peroxide, Iodine and Iodate Ion", Journal of the American Chemical Society, 1931, vol. 53, No. 01, pp. 38-44.

Bull, "Iron-Ethylenediaminetetraacetic Acid (EDTA)-Catalyzed Superoxide Dismutation Revisited : An Explanation of Why The Dismutase Activity of Fe-EDTA Cannot Be Detected in the Cytochrome c/Xanthine Oxidase Assay System", Archives of Biochemistry and Biophysics, 1982, vol. 215, No. 02, pp. 551-555, XP024804756.

Chen, "Dual Enzyme-like Activities of Iron Oxide Nanoparticles and Their Implication for Diminishing Cytotoxicity", ACS Nano, 2012, vol. 06, No. 05, pp. 4001-4012.

Day, "Catalase and Glutathione Peroxidase Mimics", Biochemical Pharmacology, 2009, vol. 77, No. 03, pp. 285-296.

Easton, "The Behaviour of Mixtures of Hydrogen Peroxide and Water. Part 1. Determination of the Densities of Mixtures of Hydrogen Peroxide and Water", Transactions of The Faraday Society, 1952, vol. 48, pp. 796-801.

Gao, "Nanocatalysts Promote Streptococcus Mutans Biofilm Matrix Degradation and Enhance Bacterial Killing to Suppress Dental Caries in Vivo", Biomaterials, 2016, vol. 101, pp. 272-284.

Koo, "A New Cost Effective Approach For Plaque Control and Tooth Decay Prevention", Penn Center for Innovation, [retrieved from the internet on Jun. 12, 2019], URL < http://upenn.technologypublisher.com/technology/22598 >, p. 1.

Livingston, "The Catalytic Decomposition of Hydrogen Peroxide in an Acid Chlorine-Chloride Solution", Journal of the American Chemical Society, 1925, vol. 47, No. 08, pp. 2069-2082.

Nardello, "Identification of The Precursor of Singlet Oxygen ($^1O_2$, $^1\Delta g$) Involved in the Disproportionation of Hydrogen Peroxide Catalyzed by Calcium Hydroxide", Chemical Communications, 1998, vol. 05, pp. 599-600.

Nardello, "Inorganic Compounds and Materials as Catalysts for Oxidations With Aqueous Hydrogen Peroxide", Journal of Molecular Catalysis. A Chemical, 2006, vol. 251, No. 1-2, pp. 185-193, XP028015283.

Rauen, "Conversion of the Synthetic Catalase Mimic Precursor TAA-1 into the Active Catalase Mimic in Isolated Hepatocytes", Chemical Biology and Drug Design, 2009, vol. 73, No. 05, pp. 494-501.

Signorella, "Bioinspired Functional Mimics of the Manganese Catalases", Coordination Chemistry Reviews, 2012, vol. 256, No. 11-12, pp. 1229-1245.

Tovmasyan, "A Comprehensive Evaluation of Catalase-Like Activity of Different Classes of Redox-Active Therapeutics", Free Radical Biology and Medicine, 2015, vol. 86, pp. 308-321.

Wahlen, "Disproportionation of Hydrogen Peroxide Into Singlet Oxygen Catalyzed by Lanthanum-Exchanged Zeolites", Journal of Catalysis, 2005, vol. 233, No. 02, pp. 422-433.

Wahlen, "Lanthanum-Doped Zinc Hydroxycarbonates for the Catalytic Disproportionation of Hydrogen Peroxide Into Singlet Oxygen", Journal of Catalysis, 2007, vol. 249, No. 01, pp. 15-23.

Walling, "The Iron(III)-Ethylenediaminetetraacetic Acid-Peroxide System", Inorganic Chemistry, 1970, vol. 09, No. 04, pp. 931-937.

Wu, "Structural, Spectroscopic, and Reactivity Models for the Manganese Catalases", Chemical Reviews, 2004, vol. 104, No. 02, pp. 903-938.

International Search Report for PCT International Application No. PCT/US2017/050052, dated Nov. 10, 2017, 5 pages.

Weichang, Mechanism of $H_2O_2$ Decomposition Catalyzed by (Ethylenediaminetetraacetato) iron (III), Journal of Catalysis, 1997, vol. 18, No. 1, pp. 83-86.

* cited by examiner

METHODS AND KITS FOR REMOVING CALCULUS USING A NON-ENZYMATIC, HYDROGEN PEROXIDE DECOMPOSITION CATALYST

CROSS REFERENCE TO RELATED APPLICATION

This application claims the benefit of U.S. Provisional Patent Application No. 62/410706, filed Oct. 20, 2016, the disclosure of which is incorporated by reference herein in its entirety.

BACKGROUND

Dental calculus may lead to periodontal diseases including gingivitis and periodontitis. The existing methods of removing dental calculus rely upon mechanical means such as scaling by trained dental professionals. Such existing removal procedures can be painful and uncomfortable for patients. In addition, the existing removal procedures can put a significant physical burden on the hygienist, often times leading to muscular and repetitive movement ailments (e.g., carpal tunnel syndrome). Moreover, a significant amount of time during the dental prophylaxis procedure is allocated to calculus removal. It is therefore desirable to create a better solution to remove calculus.

SUMMARY

Some aspects of the present disclosure provide a method of removing calculus from a tooth. The method can include applying a component A to the tooth, wherein component A includes a hydrogen peroxide or a precursor thereto; applying a component B to the tooth, wherein component B includes a non-enzymatic, hydrogen peroxide decomposition catalyst for generating oxygen gas; wherein components A and B are applied simultaneously or sequentially to the tooth, thereby generating oxygen gas to soften and/or loosen at least part of the calculus on the tooth; and removing at least a part of the calculus from the tooth.

Some aspects of the present disclosure provide a kit of parts for removing calculus from a tooth. The kit can include: a component A including a hydrogen peroxide or a precursor thereto; and a component B including a non-enzymatic, hydrogen peroxide decomposition catalyst for generating oxygen gas; and instructions for applying components A and B to the tooth simultaneously or sequentially, thereby generating oxygen gas to soften and/or loosen at least part of the calculus on the tooth, and for removing at least a part of the calculus from the tooth.

Definitions

As used in this patent application:

The term "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The words "preferred" and "preferably" refer to embodiments of the disclosure that may afford certain benefits under certain circumstances. Other embodiments may also be preferred, however, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements (e.g., preventing and/or treating an affliction means preventing, treating, or both treating and preventing further afflictions).

Herein, various sets of numerical ranges (for example, of the number of carbon atoms in a particular moiety, of the amount of a particular component, or the like) are described, and, within each set, any lower limit of a range can be paired with any upper limit of a range. Such numerical ranges also are meant to include all numbers subsumed within the range (for example, 1 to 5 includes 1, 1.5, 2, 2.75, 3, 3.80, 4, 5, and so forth).

Also herein, all numbers are assumed to be modified by the term "about" and preferably by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

The above Summary section is not intended to describe every embodiment or every implementation of the disclosure. The detailed description that follows more particularly describes illustrative embodiments. Throughout the detailed description, guidance is provided through lists of examples, which examples can be used in various combinations. In each instance, a recited list serves only as a representative group and should not be interpreted as being an exclusive list.

DETAILED DESCRIPTION

Dental calculus (also referred to as dental tartar) is defined as mineralized dental biofilm filled with crystals of various calcium phosphates or dental plaque that has partially or completely calcified. It may be caused by the continual accumulation of minerals from fluids in the oral environment on plaque on the teeth. Dental calculus is a common oral condition afflicting humans and a variety of animal species and the presence of dental calculus may lead to periodontal diseases. The existing methods of removing dental calculus, which rely upon mechanical means such as scaling, are time consuming and laborious for dental professionals, and can be a painful and unpleasant experience for patients.

The present disclosure generally relates to methods and kits of removing calculus from a tooth. Generally, the method can include applying a component A to the tooth, wherein component A includes a hydrogen peroxide or a precursor thereto; applying a component B to the tooth, wherein component B includes a non-enzymatic, hydrogen peroxide decomposition catalyst for generating oxygen gas; wherein components A and B are applied simultaneously or sequentially to the tooth, thereby generating oxygen gas to soften and/or loosen at least part of the calculus on the tooth; and removing at least a part of the calculus from the tooth. In certain embodiments, component A is applied before or after component B is applied.

The method of the present disclosure can, for example, provide an easier removal of dental calculus. In addition, the method of the present disclosure can reduce the time of calculus removal. For example, after the application of component A and component B, removing the calculus is easier and quicker. Thus, the method of the present disclosure can enable improved procedural efficiency, opportunities for more patients, additional time for other procedures and increased rest periods for the dental professional.

In some embodiments, component A can include hydrogen peroxide. The hydrogen peroxide can be generated by a peroxide generating enzyme in combination with the corresponding substrate, (e.g., glucose oxidase and Superoxide Dismutase (SOD)). For example, glucose oxidase can catalyze the oxidation of glucose to hydrogen peroxide. In some embodiments, the hydrogen peroxide may be in a form of a hydrogen peroxide adduct, such as carbamide peroxide, percarbonate salts or acids, polyvinylpyrrolidone (PVP) peroxide, or a combination thereof. Suitable percarbonate salts or acids can include, but are not limited to, percarbonic acid, sodium percarbonate, potassium percarbonate, magnesium percarbonate, calcium percarbonate, and zinc percarbonate.

In some embodiments, component A can include a hydrogen peroxide precursor, such as perborate salts or acids, metal peroxides, organic peroxides, inorganic peroxyacids or salts, or combinations thereof. Suitable perborate salts or acids can include, but are not limited to, perboric acid, sodium perborate, potassium perborate, magnesium perborate, calcium perborate, and zinc perborate. Suitable metal peroxides can include, but are not limited to, calcium peroxide and magnesium peroxide. Suitable organic peroxides can include, but are not limited to, peroxycarboxylic acids, such as peracetic acid or salts thereof, permalonic acid or salts thereof, pertartaric acid or salts thereof, and percitric acid or salts thereof. In some embodiments, the organic peroxide can be a peracetate salt. Suitable inorganic peroxyacids or salts thereof can include, but are not limited to, peroxymonosulfuric acid, peroxyphosphoric acid, and a potassium salt of a sulfuric peroxyacid.

In some embodiments, component A can include at least 1.0 molar (M) hydrogen peroxide. In some embodiments, component A can include at least 1.1 M, or at least 1.2 M, or at least 1.3 M, or at least 1.4 M, or at least 1.5 M, or at least 2.0 M, or at least 3.0 M hydrogen peroxide. In some embodiments, component A can include up to 12 M, up to 10 M, up to 8 M, up to 6 M, or up to 5 M hydrogen peroxide. In some of these embodiments, component A can include from 1.0 M to 12 M hydrogen peroxide. In some of these embodiments, component A can include from 1.5 M to 5 M hydrogen peroxide.

In some embodiments, component A can include hydrogen peroxide in an amount of 3 weight percent (wt. %), 5 wt. %, 10 wt. %, 30 wt. %, 35 wt. %, or a range between and including any two of these values. In other embodiments, component A can include a hydrogen peroxide precursor or hydrogen peroxide adduct capable of producing a similar concentration of hydrogen peroxide, for example, at least 1.5 M hydrogen peroxide. For instance, a 15 wt. % carbamide peroxide solution can produce a solution that includes 5 wt. % hydrogen peroxide.

In some embodiments, component B can include a water-soluble inorganic compound, an Fe(III) complex, a water-insoluble inorganic compound, a metalloporphyrin complex, a mononuclear metal non-porphyrin complex, a dinuclear metal non-porphyrin complex (which may be symmetric or asymmetric), a trinuclear metal non-porphyrin complex, a tetranuclear metal non-porphyrin complex, and a combination thereof.

In some embodiments, component B includes a water-soluble inorganic compound. In this context, "water-soluble" is an inorganic compound that is able to form at least 1 millimolar (mM) aqueous solution at 20° C., or is dispersible in water with primary particle sizes less than 5 nanometers (nm).

Suitable water-soluble inorganic compounds can include, but are not limited to, an iodate precursor (e.g., KI), a molybdate precursor (e.g., $Na_2MoO_4$, as disclosed in Nardello et al., *Journal of Molecular Catalysis A: Chemical*, 251(1-2), 185-193 (2006)), a polyoxometallate (e.g., $Na_{12}[WZn_3(ZnW_9O_{34})_2]$, as disclosed in Nardello et al., *Journal of Molecular Catalysis A: Chemical*, 251(1-2), 185-193 (2006)), an $HCl-Cl_2$ solution (as disclosed in Livingston et al., *Journal of the American Chemical Society*, 47(8), 2069-2082 (1925)), and a combination thereof.

Suitable iodate precursors can include, but are not limited to, iodide sources such as alkali metal iodides, alkaline earth iodides, transition metal iodides (as disclosed in Bray et al., *Journal of the American Chemical Society*, 53(1), 38-44 (1931)), or combinations thereof, most of which are soluble in water (see, e.g., https://en.wikipedia.org/wiki/Iodide). Suitable alkali metal iodides include LiI, NaI, KI, RbI, and CsI. Suitable alkaline earth iodides include $MgI_2$, $CaI_2$, and $SrI_2$. Suitable transition metal iodides include $FeI_2$ and $ZnI_2$.

In some embodiments, component B includes greater than 0.05 M, or at least 0.1 M, of an iodate precursor in water. In some embodiments, component B includes up to the solubility limit in water of an iodate precursor (e.g., 8.4 M for KI at 20° C.), but often lower, such as up to 2 M, or up to 1 M, of an iodate precursor. Typically, the concentration of the iodate precursor is below that which would stain teeth and/or produce a bad taste in the mouth of a subject.

In some embodiments, component B includes an Fe(III) complex. Suitable Fe(III) complexes include, but are not limited to, Fe(III)-ethylenediaminetetraacetic acid (i.e., Fe(III)-EDTA, as disclosed in Walling et al., *Inorganic Chemistry*, 9(4), 931-937 (1970)), FeTrF$_5$Ph-β(SO$_3$)$_2$-corrole$^{2-}$ (as disclosed in Tovmasyan et al., *Free Radic Biol Med*, 86, 308-321 (2015)), 5,14-dihydro-5,9,14,18-tetraazadi(2,2-dimethyl-[5,6]benzo-[1,3]dioxolo)[ah]cyclotetradecene-Fe(III) chloride (i.e., TAA-1/Fe(III)Cl, as disclosed in Rauen et al., *Chem Biol Drug Des*, 73(5), 494-501 (2009), and a combination thereof. The structures of such exemplary compounds are as follows:

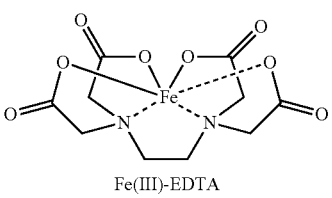

Fe(III)-EDTA

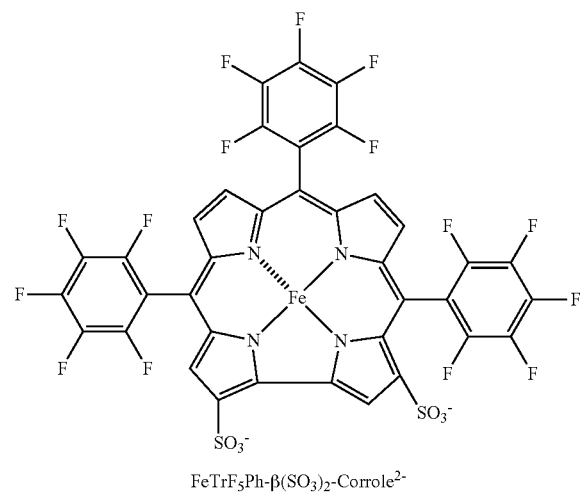

FeTrF$_5$Ph-β(SO$_3$)$_2$-Corrole$^{2-}$

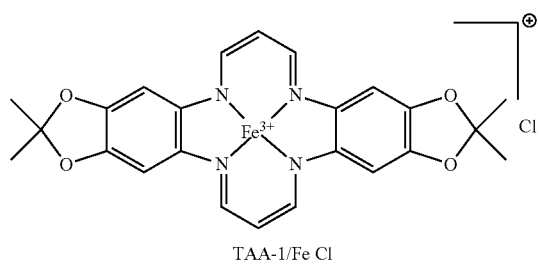

TAA-1/Fe Cl

In some embodiments, the Fe(III) complex is Fe(III)-ethylenediaminetetraacetic acid (i.e., Fe(III)-EDTA).

In some embodiments, component B includes at least 0.02 M of an Fe(III) complex. In some embodiments, component B includes up to the solubility limit in water of an Fe(III) complex. In some embodiments, component B includes up to 0.2 M of an Fe(III) complex.

In some embodiments, component B includes a water-insoluble inorganic compound. In this context, "water-insoluble" is an inorganic compound that is not able to form at least 1 millimolar (mM) aqueous solution at 20° C., or is dispersible in water with primary particle sizes greater than or equal to 5 nanometers (nm).

Suitable water-insoluble inorganic compounds include, but are not limited to, iron oxide nanoparticles (as disclosed in Chen et al., *ACS Nano*, 6(5), 4001-4012 (2012)), calcium hydroxide (as disclosed in Nardello et al., *Chemical Communications*(5), 599-600 (1998)), a lanthanum-doped zinc hydroxycarbonate (as disclosed in Wahlen et al., *Journal of Catalysis*, 249(1), 15-23 (2007)), a zeolite-supported lanthanum (e.g., LaNa-ZSM-5, as disclosed in Wahlen et al., *Journal of Catalysis*, 233(2), 422-433 (2005)), a layered double hydroxide (LDH)-supported molybdate (e.g., Mg$_x$Al$_{(1-x)}$(OH)$_2$(MoO$_4$)$_{0.5\,(1-x)}$), as disclosed in Nardello et al., *Journal of Molecular Catalysis A: Chemical*, 251(1-2), 185-193 (2006)), a clay-supported lanthanum (e.g., LaNa-montmorillonite, as disclosed in Wahlen et al., *Journal of Catalysis*, 233(2), 422-433 (2005)), and a combination thereof.

In some embodiments, component B includes a metalloporphyrin complex. Suitable metalloporphyrin complexes (i.e., porphyrinic metal complexes) include, but are not limited to, FeTE-2-PyP$^{5+}$ (as disclosed in Tovmasyan et al., *Free Radic Biol Med*, 86, 308-321 (2015)), FeTnOct-2-PyP$^{5+}$ (as disclosed in Tovmasyan et al., *Free Radic Biol Med*, 86, 308-321 (2015)), Manganese(III) tetrakis(4-benzoic acid)porphyrin chloride (i.e., MnTBAP Cl) (as disclosed in Day et al., *Biochem Pharmacol*, 77(3), 285-296 (2009)), Manganese(III) meso-tetrakis(di-N-ethylimidazole)porphyrin chloride (i.e., MnDTEIP Cl, as disclosed in Day et al., *Biochem Pharmacol*, 77(3), 285-296 (2009), or available as AEOL 10150 from Aeolus Pharmaceuticals, http://www.aolsrx.com/product-pipeline/aeol-10150), and a combination thereof. The structures of such exemplary compounds are as follows:

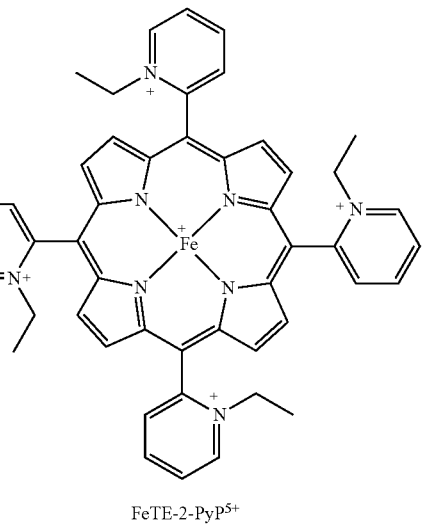

FeTE-2-PyP$^{5+}$ of the ligand $SO_3$-salpn(OH) of [Mn($SO_3$-salpn(OH))]⁻ as exemplified by the disodium salt (wherein Y=OH) is as follows:

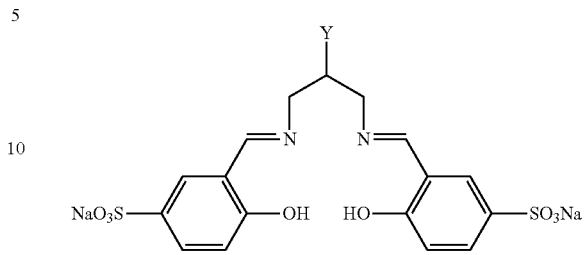

The structures of the ligands chedam and bipy of [Mn$^{II}$(chedam)(bipy)($H_2O$)] are as follows:

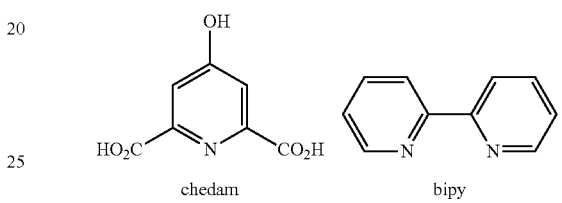

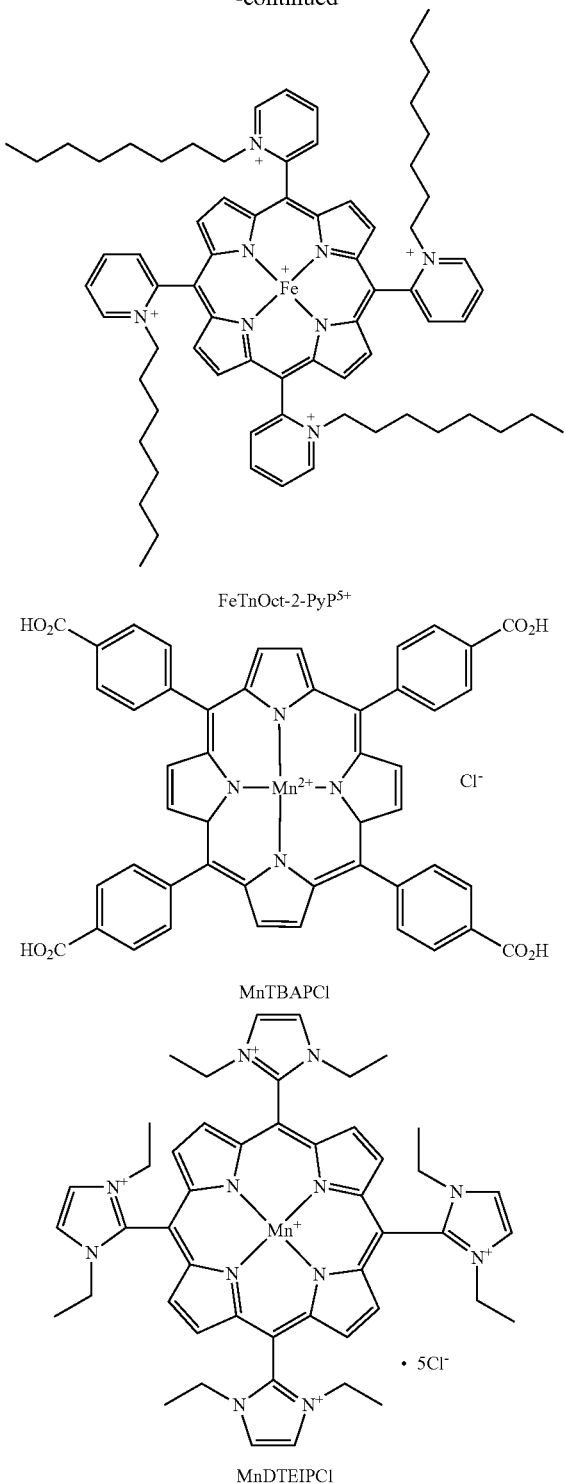

FeTnOct-2-PyP⁵⁺

MnTBAPCl

MnDTEIPCl

In some embodiments, component B includes a mononuclear metal non-porphyrin complex. Suitable mononuclear metal non-porphyrin complexes (other than the Fe(III) complexes described herein) include, but are not limited to, [Mn($SO_3$-salpn(OH))]⁻ (as disclosed in Signorella et al., *Coordination Chemistry Reviews*, 256(11-12), 1229-1245 (2012)), [Mn$^{II}$(chedam)(bipy)($H_2O$)] (as disclosed in Signorella et al., *Coordination Chemistry Reviews*, 256(11-12), 1229-1245 (2012)), and a combination thereof. The structure In some embodiments, component B includes a dinuclear metal non-porphyrin complex (which may be symmetric or asymmetric). Suitable dinuclear metal non-porphyrin complexes include, but are not limited to, [Mn(bpia)(μ-OAc)]₂ (a symmetric ligand complex, as disclosed in Wu et al., *Chemical Reviews*, 104(2), 903-938 (2004)), [Mn$^{IV}$₂(salpn)(μ-O)]₂ (a symmetric ligand complex, as disclosed in Wu et al., *Chemical Reviews*, 104(2), 903-938 (2004)), [Mn$^{III}$(2-OH-salpn)]₂ (a symmetric ligand complex, as disclosed in Wu et al., *Chemical Reviews*, 104(2), 903-938 (2004)), [Mn₂$^{II}$(μ-OAc)(μ-OH₂)(benzimpnO)]²⁺ (a symmetric ligand complex, as disclosed in Signorella et al., *Coordination Chemistry Reviews*, 256(11-12), 1229-1245 (2012)), [Mn₂(bphpmp)(μ-OAc)₂]⁺ (an asymmetric ligand complex, as disclosed in Signorella et al., *Coordination Chemistry Reviews*, 256(11-12), 1229-1245 (2012)), and a combination thereof. The structures of such exemplary compounds are as follows:

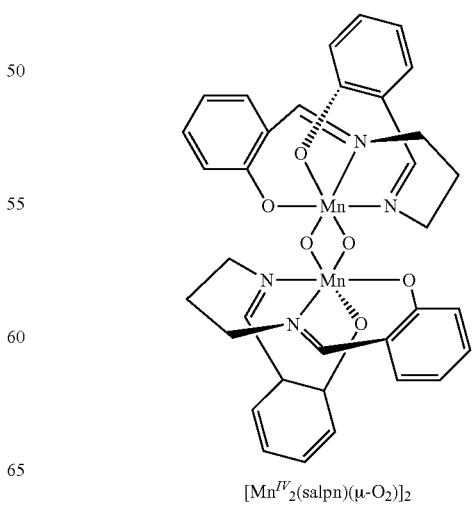

[Mn$^{IV}$₂(salpn)(μ-O₂)]₂

-continued

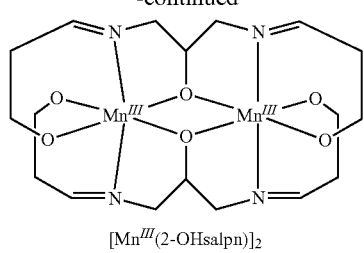

[Mn^III(2-OHsalpn)]₂

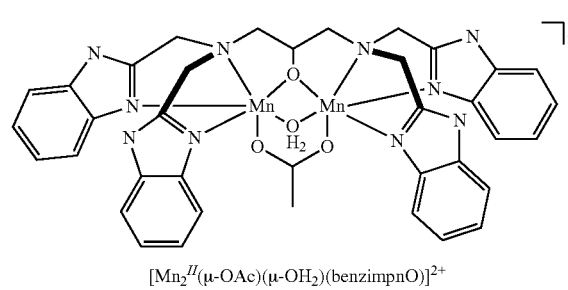

[Mn₂^II(μ-OAc)(μ-OH₂)(benzimpnO)]²⁺

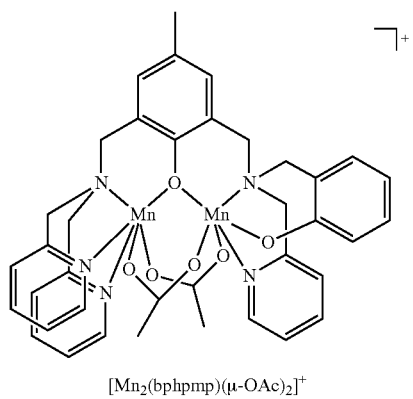

[Mn₂(bphpmp)(μ-OAc)₂]⁺

The structure of the ligand bpia of [Mn(bpia)(μ-OAc)]₂ is as follows:

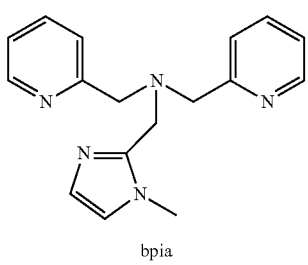 [SMILES: Cn1ccnc1CN(Cc1ccccn1)Cc1ccccn1]

bpia

In some embodiments, component B includes a trinuclear metal non-porphyrin complex. Suitable trinuclear metal non-porphyrin complexes include, but are not limited to, β-Mn^III₂Mn^II(saladhp)₂(OAc)₄(CH₃OH)₂ (as disclosed in Wu et al., *Chemical Reviews*, 104(2), 903-938 (2004)), which has the following structure:

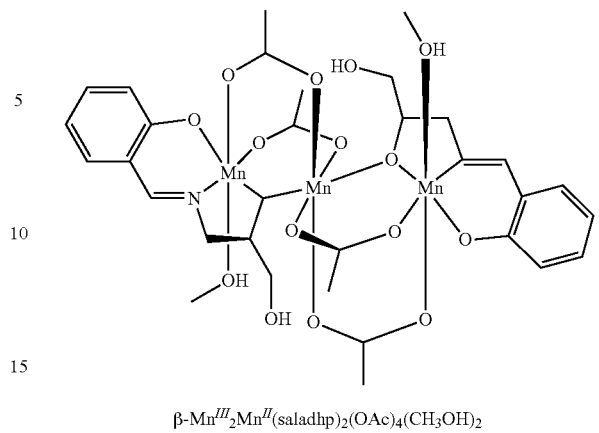

β-Mn^III₂Mn^II(saladhp)₂(OAc)₄(CH₃OH)₂

In some embodiments, component B includes a tetranuclear metal non-porphyrin complex. Suitable tetranuclear metal non-porphyrin complexes include, but are not limited to, (Ba,Ca)₂[Mn₄(μ-O)(μ-OH)(O₂—CCH₃)₂(dahpta)₂] (as disclosed in Wu et al., *Chemical Reviews*, 104(2), 903-938 (2004)), [Mn₄O₆(bpea)₄]³⁺ (as disclosed in Wu et al., *Chemical Reviews*, 104(2), 903-938 (2004)), and a combination thereof. The structures of the ligands dahpta and bpea are as follows:

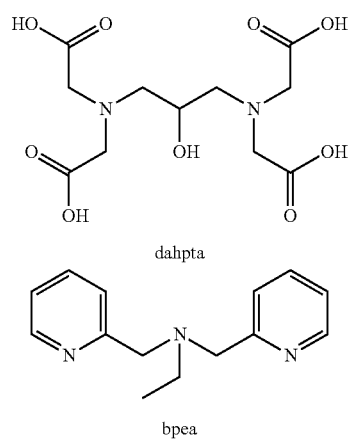

dahpta bpea

Depending on the conditions of the reaction between components A and B (i.e., the conditions under which components A and B are applied to a tooth), oxygen gas and/or free radicals may be formed. Thus, for the methods of the present disclosure, the conditions are selected such that oxygen gas is generated preferentially to free radicals. Such "conditions" include pH and the correct combination of components to form a catalyst (e.g., having EDTA in the presence of ferrous or ferric ions in solution).

In some embodiments, component B has a pH of at least 5. For certain catalysts, if the pH is too acidic, free radicals are formed. In some embodiments, component B has a pH of up to 10, or up to 9, or up to 8, or up to 7. For certain catalysts, if the pH is too basic, it may not be sufficiently safe to use in the mouth of a subject. In some embodiments, component B has a pH of 7.

The pH of component B may be adjusted through the use of a pH buffer. In some embodiments, the component B pH buffer may include compounds such as citric acid, sodium phosphate dibasic, sodium phosphate monobasic, 2,2-bis (hydroxymethyl)-2,2',2"-nitrilotriethanol, glycine, diglycine, N-[tris (hydroxymethy)methyl]glycine, N,N-bis(2-hydroxyethyl)glycine, 2-amino-2-(hydroxymethyl)-1,3-propanediol, sodium chloride, calcium chloride, potassium chloride, sodium hydroxide, and combinations thereof. In some embodiments, the pH buffer includes, but is not limited to, phosphate buffered saline, citric acid-sodium phosphate buffer, citric acid-sodium citrate buffer, bis-tris buffer (i.e., 2,2-bis(hydroxymethyl)-2,2',2"-nitrilotriethanol buffer), glycine-sodium hydroxide buffer, diglycine buffer, tricine buffer (i.e., N-[tris(hydroxymethyl)methyl]glycine buffer), bicine buffer (i.e., N,N-bis(2-hydroxyethyl) glycine buffer), and tris buffer (i.e., 2-amino-2-(hydroxymethyl)-1, 3-propanediol buffer).

Generally, in methods of the present disclosure component A is applied to the tooth surface before or after component B is applied to the tooth surface. In some embodiments, component A is applied at least 30 seconds before or after component B is applied. Either component A or component B can be (independently) in any form suitable for oral cavity delivery, such as in the form of aqueous solutions (e.g., a rinse), a gel, a paste, or a powder. For example, component A and component B can be applied both as rinses. In some embodiments, component A can be applied as a gel and component B can be applied as a rinse.

In some embodiments, methods of the present disclosure include relatively short exposure times of component A, such that no noticeable bleaching is observed by the naked eye when the method is performed, (e.g., in a single instance, and in some cases, over multiple instances).

In some embodiments, component A or component B is applied for a period of less than 1 hour, less than 30 minutes, less than 10 minutes, less than 5 minutes, less than 2 minutes, less than 1 minute, or less than 30 seconds, particularly before applying the other component. In some of these embodiments, component A or component B is applied for 10 minutes, 5 minutes, 2 minutes, 1 minute, 30 seconds, 15 seconds, or a range between and including any two of these values. In some embodiments, both component A and component B are applied for a period of less than 1 hour, less than 30 minutes, less than 10 minutes, less than 5 minutes, less than 2 minutes, or less than 1 minute.

As the hydrogen peroxide adduct or hydrogen peroxide precursor is applied to the tooth, it dissociates in the environment within the oral cavity to produce hydrogen peroxide. Hydrogen peroxide, in the presence of a non-enzymatic, hydrogen peroxide decomposition catalyst generates oxygen gas, thereby softening and/or loosening the calculus on the tooth. The generated oxygen gas can, for example, weaken the adhesion between the calculus and tooth surface so that the calculus can be removed easily after relatively short exposure times to component A and component B. In some embodiments, the generated oxygen gas can soften and/or loosen the calculus so that the removal of the calculus, for example, by hand scaling is much easier. For instance, the calculus can be removed in a shorter time or with a less force.

After component A and component B are applied, at least a part of the calculus can be removed from the tooth by a suitable mechanical means, (e.g., scaling (such as using a dental scaler), brushing, swabbing, wiping, ultrasonic scaling, air polishing or jetted water). In some embodiments, part of the calculus may be removed by mechanical means other than tooth brushing, for example, by a dental scaler. In some embodiments, the removing step occurs within 1 day, 12 hours, 6 hours, 3 hours, 1 hour, 30 minutes, 10 minutes, 5 minutes, 2 minutes, 1 minute, 30 seconds, or 15 seconds, after the applying steps. In some embodiments, the removing step lasts for a period less than 10 minutes, less than 5 minutes, less than 2 minutes, or less than 1 minute. In other embodiments, the removing step lasts 10 minutes, 5 minutes, 2 minutes, 1 minute, 30 seconds, or a range between and including any two of these values. Thus, the method of the present disclosure can, for example, provide an easier and/or quicker removal of the calculus. In some embodiments, the applying steps and removing step are all completed in less than 1 day, less than 12 hours, less than 6 hours, less than 3 hours, less than 1 hour, less than 30 minutes, less than 10 minutes, less than 5 minutes, less than 2 minutes, or less than 1 minute.

In an exemplary embodiment, first a non-enzymatic, hydrogen peroxide decomposition catalyst for generating oxygen gas is applied to a tooth surface that includes calculus. After one minute, a hydrogen peroxide aqueous rinse solution is applied to the tooth surface. After about 15 seconds, the calculus is hand scaled.

In some embodiments, additives can be applied to the tooth surface. In some embodiments, additives can be applied with component A and/or component B. The additives used in the method can include, but are not limited to, antiseptics and preservatives, antibiotics, flavoring materials, surfactants, abrasives, thickeners and binders, propellants, carriers, tartar control agents, calcium sequestrants, fluoride salts, and dyes.

Suitable antiseptics and preservatives can include, but are not limited to, chlorhexidine and salts thereof, polyhexamethylene biguanide, octenidine, quaternary ammonium salts and polymers thereof, organic acids, chelating agents, for example, a calcium chelating agent (e.g., ethylenediaminetetraacetic acid (EDTA)), essential oils, and parabens. Non-limiting examples of antibiotics can include penicillin, tetracycline, minocycline, and the like. Examples of antibiotics can also include those described in U.S. Pat. No. 6,685,921 (Lawlor). Examples of flavoring materials can include artificial sweeteners, plant oils, and synthetic flavors. Examples of abrasives can include silica particles, synthetic inorganic particles, and synthetic or plant derived organic particles. Suitable surfactants can include those described in U.S. Pat. Pub. No. 2006/0051385 (Scholz). Examples of such surfactants include cationic surfactants, zwitterionic surfactants, nonionic surfactants, and anionic surfactants. Examples of thickeners can include glycerol, silica, cellulose-based polymers, plant gums (e.g., guar and xanthan gum), petroleum derived materials such as petrolatum, polyethylene glycols, polyvinyl pyrrolidone and copolymers thereof, polylactic acids, long chain fatty acid alcohols, and acrylate polymers. Suitable binders can include those described in U.S. Pat. No. 8,647,608 (Yang et al.). Suitable carriers can include those described in U.S. Pat. No. 8,647,608 (Yang et al.). Carriers can include any alcohols suitable for use in a subject's oral cavity, including ethanol, isopropanol, and glycerol. Suitable dyes include those conventionally used in dental products. Examples of tartar control agents can include those described in U.S. Pat. No. 6,685,921 (Lawlor). Anti-tartar agents known for use in dental care products can include, but are not limited to phosphate. Phosphates can include pyrophosphates, polyphosphates, polyphosphonates, and mixtures thereof. Pyrophosphate salts can include the dialkali metal pyrophosphate salts, tetra-alkali metal pyrophosphate salts, and mixtures thereof. Examples of fluoride salts can include those described in U.S. Pat. No. 6,685,921 (Lawlor), U.S. Pat. No. 3,535,421 (Briner et al.), and U.S. Pat. No. 3,678,154 (Briner et al.).

The kits of removing calculus from a tooth of the present disclosure can include a component A including a hydrogen peroxide or a precursor thereto; and a component B including a non-enzymatic, hydrogen peroxide decomposition catalyst for generating oxygen gas; and instructions for applying components A and B to the tooth simultaneously or sequentially, thereby generating oxygen gas to soften and/or loosen at least part of the calculus on the tooth, and for removing at least a part of the calculus from the tooth. In such kits, component A and/or component B may further include one or more additives as described herein.

EMBODIMENTS

The following embodiments are intended to be illustrative of the present disclosure and not limiting.

Embodiment 1 is a method of removing calculus from a tooth comprising: applying a component A to the tooth, wherein component A comprises a hydrogen peroxide or a precursor thereto; applying a component B to the tooth, wherein component B comprises a non-enzymatic, hydrogen peroxide decomposition catalyst for generating oxygen gas; wherein components A and B are applied simultaneously or sequentially to the tooth, thereby generating oxygen gas to soften and/or loosen at least part of the calculus on the tooth; and removing at least a part of the calculus from the tooth.

Embodiment 2 is the method of embodiment 1 wherein component A is applied before or after component B is applied.

Embodiment 3 is the method of embodiment 1 or 2 wherein component A comprises at least 1.0 M, or at least 1.1 M, or at least 1.2 M, or at least 1.3 M, or at least 1.4 M, or at least 1.5 M, or at least 2.0 M, or at least 3.0 M hydrogen peroxide.

Embodiment 4 is the method of any one of embodiments 1 to 3 wherein component A comprises up to 12 M, or up to 5 M hydrogen peroxide.

Embodiment 5 is the method of any one of embodiments 1 to 4 wherein the hydrogen peroxide is a hydrogen peroxide adduct.

Embodiment 6 is the method of embodiment 5 wherein the hydrogen peroxide adduct is selected from the group of carbamide peroxide, percarbonate salts or acids, polyvinylpyrrolidone (PVP) peroxide, and a combination thereof.

Embodiment 7 is the method of any one of embodiments 1 to 4 wherein the hydrogen peroxide precursor is selected from the group of perborate salts or acids, metal peroxides, organic peroxides, inorganic peroxyacids or salts, and combinations thereof.

Embodiment 8 is the method of embodiment 7 wherein the precursor is an organic peroxide, and wherein the organic peroxide is peracetic acid or a salt thereof.

Embodiment 9 is the method of any one of embodiments 1 to 4 wherein the hydrogen peroxide is generated by a peroxide generating enzyme.

Embodiment 10 is the method of embodiment 9 wherein the peroxide generating enzyme is glucose oxidase.

Embodiment 11 is the method of any one of embodiments 1 to 10 wherein component B comprises a water-soluble inorganic compound, an Fe(III) complex, a water-insoluble inorganic compound, a metalloporphyrin complex, a mononuclear metal non-porphyrin complex, a dinuclear metal non-porphyrin complex (which may be symmetric or asymmetric), a trinuclear metal non-porphyrin complex, a tetranuclear metal non-porphyrin complex, and a combination thereof.

Embodiment 12 is the method of embodiment 11 wherein component B comprises a water-soluble inorganic compound.

Embodiment 13 is the method of embodiment 12 wherein the water-soluble inorganic compound is selected from the group of an iodate precursor (e.g., KI), a molybdate precursor (e.g., $Na_2MoO_4$), a polyoxometallate (e.g., $Na_{12}[WZn_3(ZnW_9O_{34})_2]$), an $HCl$—$Cl_2$ solution, and a combination thereof.

Embodiment 14 is the method of embodiment 13 wherein the water-soluble inorganic compound comprises an iodate precursor.

Embodiment 15 is the method of embodiment 14 wherein the iodate precursor comprises an iodide source.

Embodiment 16 is the method of embodiment 15 wherein the iodide source is selected from the group of an alkali metal iodide (e.g., LiI, NaI, KI, RbI, CsI), an alkaline earth iodide (e.g., $MgI_2$, $CaI_2$, $SrI_2$), a transition metal iodide (e.g., $FeI_2$, $ZnI_2$), and a combination thereof.

Embodiment 17 is the method of any one of embodiments 14 to 16 wherein component B comprises greater than 0.05 M of an iodate precursor.

Embodiment 18 is the method of embodiment 17 wherein component B comprises at least 0.1 M of an iodate precursor.

Embodiment 19 is the method of any one of embodiments 12 to 14 wherein component B comprises up to the solubility limit of an iodate precursor (e.g., 8.4 M for KI at 20° C.).

Embodiment 20 is the method of embodiment 19 wherein component B comprises up to 2 M of an iodate precursor.

Embodiment 21 is the method of embodiment 20 wherein component B comprises up to 1 M of an iodate precursor.

Embodiment 22 is the method of embodiment 11 wherein component B comprises an Fe(III) complex.

Embodiment 23 is the method of embodiment 22 wherein the Fe(III) complex is selected from the group of Fe(III)-ethylenediaminetetraacetic acid (i.e., Fe(III)-EDTA), $FeTrF_5Ph$-$\beta(SO_3)_2$-corrole$^{2-}$, 5,14-dihydro-5,9,14,18-tetraaza-di(2,2-dimethyl[5,6]benzo-[1,3]dioxolo)[a,h]cyclotetradecene-Fe(III) chloride (i.e., TAA-1/Fe(III)Cl), and a combination thereof.

Embodiment 24 is the method of embodiment 23 wherein the Fe(III) complex is Fe(III)-ethylenediaminetetraacetic acid (Fe(III)-EDTA).

Embodiment 25 is the method of any one of embodiments 22 to 24 wherein component B comprises at least 0.02 M of an Fe(III) complex.

Embodiment 26 is the method of any one of embodiments 22 to 25 wherein component B comprises up to 0.2 M of an Fe(III) complex.

Embodiment 27 is the method of embodiment 11 wherein component B comprises a water-insoluble inorganic compound.

Embodiment 28 is the method of embodiment 27 wherein the water-insoluble inorganic compound is selected from the group of iron oxide nanoparticles, calcium hydroxide, a lanthanum-doped zinc hydroxycarbonate, a zeolite-supported lanthanum (e.g., LaNa-ZSM-5), a layered double hydroxide (LDH)-supported molybdate (e.g., $Mg_xAl_{(1-x)}(OH)_2(MoO_4)_{0.5(1-x)}$), a clay-supported lanthanum (e.g., LaNa-montmorillonite), and a combination thereof.

Embodiment 29 is the method of embodiment 11 wherein component B comprises a metalloporphyrin complex.

Embodiment 30 is the method of embodiment 29 wherein the metalloporphyrin complex (i.e., porphyrinic metal complex) is selected from the group of FeTE-2-PyP$^{5+}$, FeTnOct-2-PyP$^{5+}$, Manganese(III) tetrakis(4-benzoic acid)porphyrin chloride (i.e., MnTBAP Cl), Manganese(III) mesotetrakis(di-N-ethylimidazole)porphyrin chloride (i.e., MnDTEIP Cl or AEOL 10150), and a combination thereof.

Embodiment 31 is the method of embodiment 11 wherein component B comprises a mononuclear metal non-porphyrin complex.

Embodiment 32 is the method of embodiment 31 wherein the mononuclear metal non-porphyrin complex (other than the Fe(III) complexes described herein) is selected from the group of [Mn(SO$_3$-salpn (OH))]$^-$, [Mn$^{II}$(chedam)(bipy)(H$_2$O)], and a combination thereof.

Embodiment 33 is the method of embodiment 11 wherein component B comprises a dinuclear metal non-porphyrin complex.

Embodiment 34 is the method of embodiment 33 wherein the dinuclear metal non-porphyrin complex is selected from the group of [Mn(bpia)(µ-OAc)]$_2$, [Mn$^{IV}_2$(salpn)(µ-O)]$_2$, [Mn$^{III}$(2-OHsalpn)]$_2$, [Mn$_2^{II}$(µ-OAc)(µ-OH$_2$)(benzimpnO)]$^{2+}$, [Mn$_2$(bphpmp)(µ-OAc)$_2$]$^+$, and a combination thereof.

Embodiment 35 is the method of embodiment 11 wherein component B comprises a trinuclear metal non-porphyrin complex.

Embodiment 36 is the method of embodiment 35 wherein the trinuclear metal non-porphyrin complex is β-Mn$^{III}_2$Mn$^{II}$(saladhp)$_2$(OAc)$_4$(CH$_3$OH)$_2$.

Embodiment 37 is the method of embodiment 11 wherein component B comprises a tetranuclear metal non-porphyrin complex.

Embodiment 38 is the method of embodiment 37 wherein the tetranuclear metal non-porphyrin complex is selected from the group of (Ba,Ca)$_2$[Mn$_4$(µ-O)(µ-OH)(O$_2$—CCH$_3$)$_2$(dahpta)$_2$], [Mn$_4$O$_6$(bpea)$_4$]$^{3+}$, and a combination thereof.

Embodiment 39 is the method of any one of embodiments 1 to 38 wherein component B has a pH of at least 5.

Embodiment 40 is the method of any one of embodiments 1 to 39 wherein component B has a pH of up to 10 (or up to 9, or up to 8, or up to 7).

Embodiment 41 is the method of any of embodiments 1 to 40 wherein component B comprises a pH buffer.

Embodiment 42 is the method of embodiment 41 wherein the component B buffer comprises compounds selected from citric acid, sodium phosphate dibasic, sodium phosphate monobasic, 2,2-bis (hydroxymethyl)-2,2',2"-nitrilotriethanol, glycine, diglycine, N-[tris(hydroxymethyl)methyl]glycine, N,N-bis(2-hydroxyethyl)glycine, 2-amino-2-(hydroxymethyl)-1,3-propanediol, sodium chloride, calcium chloride, potassium chloride, sodium hydroxide, and combinations thereof.

Embodiment 43 is the method of embodiment 42 wherein the buffer is selected from the group of phosphate buffered saline, citric acid-sodium phosphate buffer, citric acid-sodium citrate buffer, bis-tris buffer (i.e., 2,2-bis(hydroxymethyl)-2,2',2"-nitrilotriethanol buffer), glycine-sodium hydroxide buffer, diglycine buffer, tricine buffer (i.e., N-[tris(hydroxymethyl)methyl]glycine buffer), bicine buffer (i.e., N,N-bis(2-hydroxyethyl)glycine buffer), and tris buffer (i.e., 2-amino-2-(hydroxymethyl)-1,3-propanediol buffer).

Embodiment 44 is the method of any of embodiments 2 to 43 wherein component A is applied at least 30 seconds before applying component B.

Embodiment 45 is the method of any of embodiments 2 to 44 wherein component A is applied for a period of less than 1 hour before applying component B.

Embodiment 46 is the method of embodiment 45 wherein component A is applied for a period of less than 30 minutes before applying component B.

Embodiment 47 is the method of embodiment 46 wherein component A is applied for a period of less than 1 minute before applying component B.

Embodiment 48 is the method of embodiment 47 wherein component A is applied for a period of less than 30 seconds before applying component B.

Embodiment 49 is the method of any of embodiments 2 to 43 wherein component B is applied at least 30 seconds before applying component A.

Embodiment 50 is the method of any of embodiments 2 to 43 and embodiment 49 wherein component B is applied for a period of less than 1 hour before applying component A.

Embodiment 51 is the method of embodiment 50 wherein component B is applied for a period of less than 30 minutes before applying component A.

Embodiment 52 is the method of embodiment 51 wherein component B is applied for a period of less than 1 minute before applying component A.

Embodiment 53 is the method of embodiment 52 wherein component B is applied for a period of less than 30 seconds before applying component A.

Embodiment 54 is the method of any of embodiments 1 to 53 wherein both component A and component B are applied for a period of less than 1 hour.

Embodiment 55 is the method of any of embodiments 1 to 54 wherein the removing step occurs within 1 day after the applying steps.

Embodiment 56 is the method of any of embodiments 1 to 55 wherein the applying steps and removing step are all completed in less than 1 day.

Embodiment 57 is the method of any of embodiments 1 to 56 wherein at least a part of the calculus is removed by mechanical means.

Embodiment 58 is the method of embodiment 57 wherein at least a part of the calculus is removed by mechanical means other than tooth brushing.

Embodiment 59 is the method of embodiment 57 or 58 wherein at least a part of the calculus is removed by a dental scaler.

Embodiment 60 is a kit of parts for removing calculus from a tooth comprising: a component A comprising a hydrogen peroxide or a precursor thereto; and a component B comprising a non-enzymatic, hydrogen peroxide decomposition catalyst for generating oxygen gas; and instructions for applying components A and B to the tooth simultaneously or sequentially, thereby generating oxygen gas to soften and/or loosen at least part of the calculus on the tooth, and for removing at least a part of the calculus from the tooth.

Embodiment 61 is the kit of parts of embodiment 60 wherein component A and/or component B further includes one or more additives.

Embodiment 62 is the kit of parts of embodiment 61 wherein the one or more additives are selected from antiseptics and preservatives, antibiotics, flavoring materials, surfactants, abrasives, thickeners and binders, propellants, carriers, tartar control agents, calcium sequestrants, fluoride salts, and dyes.

EXAMPLES

The following examples are given to illustrate, but not limit, the scope of this invention. As used herein, all parts and percentages are by weight unless otherwise specified. All commercial materials were used as obtained from the vendor. Unless otherwise specified, materials can be obtained from Sigma-Aldrich Corp. (St. Louis, Mo.).

Materials and Methods

Hydrogen peroxide ($H_2O_2$), in the form of a 30 wt. % aqueous solution, was obtained from Avantor Performance Materials (Center Valley, Pa.) or Acros Organics (Geel, Belgium). Diluted aqueous hydrogen peroxide solutions (about 3 M, 1.5 M, and 0.3 M) were prepared using either deionized or distilled water. The molarity of each aqueous hydrogen peroxide solution at room temperature (about 23° C.) was calculated from the weight percent and approximate density of the solution (densities were calculated at 25° C. using Equation (3) in Easton, M. F., Mitchell, A. G., Wynne-Jones, W. F. K., "The Behaviour of Mixtures of Hydrogen Peroxide and Water. Part I. Determination of the Densities of Mixtures of Hydrogen Peroxide and Water", Trans. Faraday Soc., 48, 796 (1952)).

Potassium iodide was obtained from EM Science (Gibbstown, N.J.) and was dissolved into deionized water to prepare 1 M and 0.1 M solutions.

Ethylenediaminetetraacetic acid iron (III) sodium salt (NaFeEDTA) was obtained from Sigma-Aldrich Corporation. The NaFeEDTA solutions (0.2 M, 0.025 M, and 0.01 M) were prepared in 0.2 M phosphate buffer solution (PBS), pH 7.9.

Extracted human teeth containing multiple regions with calculus deposits (available from various suppliers such as enretec GmbH, Velten, Germany) were stored in 0.5-1.0 wt. % aqueous chloramine-T solution prior to use. To prepare the extracted teeth for calculus removal testing, each tooth was rinsed with deionized water. Hand scaling of calculus deposits as described in the following examples was performed using a universal (i.e., Columbia) curette commercially available from OSUNG MND CO., LTD. (Korea).

Example 1

A region of calculus on an extracted tooth was treated with deionized water. A portion of the region was hand scaled and this was identified as the control portion of the calculus region.

To an unscaled portion on the same region of calculus on the tooth, 2-3 drops of NaFeEDTA (0.2 M) solution was applied, followed 15 seconds later by the application of 2-3 drops of hydrogen peroxide (10 wt. %, about 3 M) solution. After waiting approximately 30 seconds, hand scaling of this portion was performed. This was identified as the treatment portion of the calculus region.

A noticeable improvement in the ease of calculus removal by hand scaling was observed for the treatment portion of the calculus region when compared with the control portion of the calculus region.

Example 2

A region of calculus on an extracted tooth was treated with deionized water. A portion of the region was hand scaled and this was identified as the control portion of the calculus region.

To an unscaled portion on the same region of calculus on the tooth, 2-3 drops of NaFeEDTA (0.025 M) solution was applied, followed immediately by the application of 2-3 drops of hydrogen peroxide (10 wt. %, about 3 M) solution. After waiting approximately 30 seconds, hand scaling of this portion was performed. This was identified as the treatment portion of the calculus region.

A noticeable improvement in the ease of calculus removal by hand scaling was observed for the treatment portion of the calculus region when compared with the control portion of the calculus region.

Example 3

A region of calculus on an extracted tooth was treated with deionized water. A portion of the region was hand scaled and this was identified as the control portion of the calculus region.

To an unscaled portion on the same region of calculus on the tooth, 2-3 drops of potassium iodide (1 M) solution was applied, followed immediately by the application of 2-3 drops of hydrogen peroxide (10 wt. %, about 3 M) solution. After waiting approximately 30 seconds, hand scaling of this portion was performed. This was identified as the treatment portion of the calculus region.

A noticeable improvement in the ease of calculus removal by hand scaling was observed for the treatment portion of the calculus region when compared with the control portion of the calculus region.

Example 4

A region of calculus on an extracted tooth was treated with deionized water. A portion of the region was hand scaled and this was identified as the control portion of the calculus region.

To an unscaled portion on the same region of calculus on the tooth, 2-3 drops of potassium iodide (0.1 M) solution was applied, followed immediately by the application of 2-3 drops of hydrogen peroxide (10 wt. %, about 3 M) solution. After waiting approximately 30 seconds, hand scaling of this portion was performed. This was identified as the treatment portion of the calculus region.

A noticeable improvement in the ease of calculus removal by hand scaling was observed for the treatment portion of the calculus region when compared with the control portion of the calculus region.

Example 5

A region of calculus on an extracted tooth was treated with deionized water. A portion of the region was hand scaled and this was identified as the control portion of the calculus region.

To an unscaled portion on the same region of calculus on the tooth, 2-3 drops of potassium iodide (1 M) solution was applied, followed 15 seconds later by the application of 2-3 drops of hydrogen peroxide (5 wt. %, about 1.5 M) solution. After waiting approximately 30 seconds, hand scaling of this portion was performed. This was identified as the treatment portion of the calculus region.

A noticeable improvement in the ease of calculus removal by hand scaling was observed for the treatment portion of the calculus region when compared with the control portion of the calculus region.

Comparative Example 1

A region of calculus on an extracted tooth was treated with deionized water. A portion of the region was hand scaled and this was identified as the control portion of the calculus region.

To an unscaled portion on the same region of calculus on the tooth, 2-3 drops of NaFeEDTA (0.2 M) solution was applied, followed 15 seconds later by the application of 2-3 drops of hydrogen peroxide (1 wt. %, about 0.3 M) solution. After waiting approximately 30 seconds, hand scaling of this portion was performed. This was identified as the treatment portion of the calculus region.

No noticeable improvement in the ease of calculus removal by hand scaling was observed for the treatment portion of the calculus region when compared with the control portion of the calculus region.

Comparative Example 2

A region of calculus on an extracted tooth was treated with deionized water. A portion of the region was hand scaled and this was identified as the control portion of the calculus region.

To an unscaled portion on the same region of calculus on the tooth, 2-3 drops of NaFeEDTA (0.01 M) solution was applied, followed 15 seconds later by the application of 2-3 drops of hydrogen peroxide (10 wt. %, about 3 M) solution. After waiting approximately 30 seconds, hand scaling of this portion was performed. This was identified as the treatment portion of the calculus region.

No noticeable improvement in the ease of calculus removal by hand scaling was observed for the treatment portion of the calculus region when compared with the control portion of the calculus region.

The referenced descriptions contained in the patents, patent documents, and publications cited herein are incorporated by reference in their entirety as if each were individually incorporated. Various unforeseeable modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only, with the scope of the disclosure intended to be limited only by the claims set forth herein as follows.

What is claimed is:

1. A method of removing calculus from a tooth comprising:
    applying a component A to the tooth, wherein component A comprises a hydrogen peroxide or a precursor thereto;
    applying a component B to the tooth, wherein component B comprises a non-enzymatic, hydrogen peroxide decomposition catalyst for generating oxygen gas;
    wherein components A and B are applied simultaneously or sequentially to the tooth, thereby generating oxygen gas to soften and/or loosen at least part of the calculus on the tooth; and
    removing at least a part of the calculus from the tooth.

2. The method of claim 1 wherein component A is applied before or after component B is applied.

3. The method of claim 2 wherein component A is applied for a period of less than 1 hour before applying component B.

4. The method of claim 2 wherein component B is applied for a period of less than 1 hour before applying component A.

5. The method of claim 1 wherein component B comprises a water-soluble inorganic compound, an Fe(III) complex, a water-insoluble inorganic compound, a metalloporphyrin complex, a mononuclear metal non-porphyrin complex, a dinuclear metal non-porphyrin complex, a trinuclear metal non-porphyrin complex, a tetranuclear metal non-porphyrin complex, and a combination thereof.

6. The method of claim 5 wherein Component B comprises a water-soluble inorganic compound.

7. The method of claim 6 wherein the water-soluble inorganic compound is selected from the group of an iodate precursor, a molybdate precursor, a polyoxometallate, an $HCl-Cl_2$ solution, and a combination thereof.

8. The method of claim 7 wherein component B comprises greater than 0.05 M of an iodate precursor.

9. The method of claim 5 wherein component B comprises an Fe(III) complex.

10. The method of claim 9 wherein component B comprises at least 0.02 M of an Fe(III) complex.

11. The method of claim 9 wherein the Fe(III) complex is selected from the group of Fe(III)-ethylenediaminetetraacetic acid, $FeTrF_5Ph-\beta(SO_3)_2$-corrole$^{2-}$, 5,14-dihydro-5,9,14,18-tetraaza-di(2,2-dimethyl-[5,6]benzo-[1,3]dioxolo)[a,h]cyclotetradecene-Fe(III) chloride, and a combination thereof.

12. The method of claim 11 wherein the Fe(III) complex is Fe(III)-ethylenediaminetetraacetic acid.

13. The method of claim 1 wherein component B has a pH of at least 5 up to 10.

14. The method of claim 13 wherein component B comprises a pH buffer.

15. The method of claim 14 wherein the component B buffer comprises compounds selected from citric acid, sodium phosphate dibasic, sodium phosphate monobasic, 2,2-bis(hydroxymethyl)-2,2',2"-nitrilotriethanol, glycine, diglycine, N-[tris(hydroxymethyl)methyl]glycine, N,N-bis(2-hydroxyethyl) glycine, 2-amino-2-(hydroxymethyl)-1,3-propanediol, sodium chloride, calcium chloride, potassium chloride, sodium hydroxide, and combinations thereof.

16. The method of claim 1 wherein component A comprises at least 1.0 M hydrogen peroxide.

17. The method of claim 1 wherein at least a part of the calculus is removed by mechanical means.

18. A kit of parts for removing calculus from a tooth comprising:
    a component A comprising a hydrogen peroxide or a precursor thereto; and
    a component B comprising a non-enzymatic, hydrogen peroxide decomposition catalyst for generating oxygen gas; and
    instructions for applying component A and component B to the tooth according to the method of claim 1.

19. The kit of parts of claim 18 wherein component A and/or component B further includes one or more additives.

20. The kit of parts of claim 19 wherein one or more additives are selected from antiseptics and preservatives, antibiotics, flavoring materials, surfactants, abrasives, thickeners and binders, propellants, carriers, tartar control agents, calcium sequestrants, fluoride salts, and dyes.

* * * * *